(12) United States Patent
Furutani et al.

(10) Patent No.: US 10,950,910 B2
(45) Date of Patent: Mar. 16, 2021

(54) AIR CELL AND PATCH

(71) Applicant: MAXELL HOLDINGS, LTD., Kyoto (JP)

(72) Inventors: Takahiro Furutani, Kyoto (JP);
Kunihiko Koyama, Kyoto (JP);
Mitsutoshi Watanabe, Kyoto (JP);
Hiroaki Ono, Kyoto (JP)

(73) Assignee: Maxell Holdings, Ltd., Kyoto (JP)

( * ) Notice: Subject to any disclaimer, the term of this patent is extended or adjusted under 35 U.S.C. 154(b) by 208 days.

(21) Appl. No.: 16/331,337

(22) PCT Filed: Sep. 20, 2017

(86) PCT No.: PCT/JP2017/033912
§ 371 (c)(1),
(2) Date: Mar. 7, 2019

(87) PCT Pub. No.: WO2018/056307
PCT Pub. Date: Mar. 29, 2018

(65) Prior Publication Data
US 2019/0363412 A1    Nov. 28, 2019

(30) Foreign Application Priority Data

Sep. 20, 2016  (JP) ................................ 2016-182814
Mar. 6, 2017   (JP) ................................ 2017-041205
(Continued)

(51) Int. Cl.
*H01M 12/06*   (2006.01)
*H01M 12/02*   (2006.01)
*A61B 5/00*    (2006.01)

(52) U.S. Cl.
CPC ........... *H01M 12/06* (2013.01); *H01M 12/02* (2013.01); *A61B 5/6833* (2013.01); *A61B 2560/0214* (2013.01); *H01M 2300/0025* (2013.01)

(58) Field of Classification Search
CPC .............................. H01M 12/06; H01M 12/02
See application file for complete search history.

(56) References Cited

U.S. PATENT DOCUMENTS

2007/0077485 A1   4/2007 Takamura et al.
2010/0121306 A1   5/2010 Yodfat et al.
(Continued)

FOREIGN PATENT DOCUMENTS

JP   2001-307746 A   11/2001
JP   2006-19246 A    1/2006
(Continued)

OTHER PUBLICATIONS

International Search Report for PCT/JP2017/033912 dated Oct. 17, 2017.
(Continued)

*Primary Examiner* — Stewart A Fraser
(74) *Attorney, Agent, or Firm* — Birch, Stewart, Kolasch & Birch, LLP

(57) ABSTRACT

Provided are an air cell that has a reduced environmental impact and has favorable discharge characteristics as well as a patch equipped with the air cell. An air cell of the present invention includes, an outer case, which contains a positive electrode having a catalyst layer containing a catalyst and a binder, a negative electrode containing a metal material, a separator, and an electrolytic solution. The electrolytic solution is an aqueous solution with a pH of 3 or more and less than 12. The separator has an air permeability of 10 sec/100 ml or more, or the positive electrode has a porous sheet made (Continued)

of carbon as a current collector. A patch of the present invention includes the air cell of the present invention as a power supply.

20 Claims, 1 Drawing Sheet

(30) Foreign Application Priority Data

| | | |
|---|---|---|
| Mar. 9, 2017 | (JP) | 2017-044497 |
| Jul. 4, 2017 | (JP) | 2017-130902 |
| Aug. 10, 2017 | (JP) | 2017-154905 |

(56) References Cited

U.S. PATENT DOCUMENTS

| | | |
|---|---|---|
| 2010/0191078 A1 | 7/2010 | Yodfat et al. |
| 2010/0198187 A1 | 8/2010 | Yodfat et al. |
| 2013/0078537 A1* | 3/2013 | Jorissen ............ H01M 4/8882 |
| | | 429/405 |
| 2013/0304018 A1 | 11/2013 | Yodfat et al. |
| 2013/0310800 A1 | 11/2013 | Yodfat et al. |
| 2014/0220459 A1 | 8/2014 | Iida et al. |
| 2016/0106914 A1 | 4/2016 | Yodfat et al. |
| 2016/0183794 A1 | 6/2016 | Gannon et al. |
| 2016/0190668 A1* | 6/2016 | Satou ................ H01M 2/024 |
| | | 429/403 |
| 2017/0104254 A1 | 4/2017 | Hattori et al. |
| 2017/0237135 A1 | 8/2017 | Iida et al. |
| 2017/0352936 A1* | 12/2017 | Jin ................ H01M 12/06 |
| 2018/0264192 A1 | 9/2018 | Yodfat et al. |

FOREIGN PATENT DOCUMENTS

| | | |
|---|---|---|
| JP | 2010-534084 A | 11/2010 |
| JP | 2013-20797 A | 1/2013 |
| JP | 2014-154225 A | 8/2014 |
| JP | 2014-165099 A | 9/2014 |
| JP | 2015-53136 A | 3/2015 |
| JP | 2016-46116 A | 4/2016 |
| JP | 2016-146257 A | 8/2016 |
| WO | WO 2009/013733 A2 | 1/2009 |
| WO | WO 2009/013734 A2 | 1/2009 |
| WO | WO 2009/013735 A1 | 1/2009 |
| WO | WO 2016/006292 A1 | 1/2016 |

OTHER PUBLICATIONS

European Patent Office Communication issued in the corresponding European Patent Application No. 17853077.0 dated Jun. 30, 2020.

* cited by examiner

AIR CELL AND PATCH

TECHNICAL FIELD

The present invention relates to an air cell that has a reduced environmental impact and has favorable discharge characteristics, and a patch equipped with the air cell.

BACKGROUND ART

The application of air cells has recently been needed in increasing number of fields, the air cells having a positive electrode formed of an air electrode in which manganese oxide, carbon, or the like is used as a catalyst, and having a negative electrode in which a metal material, such as zinc-based particles including zinc particles, zinc alloy particles, and the like, is used as an active material, and accordingly, there is demand for various improvements to the air cells.

One such required improvement to air cells is to reduce their environmental impact. Although application of air cells to power supplies of various types of sensors for use with the body, such as a body temperature patch, golf head velocity sensors, and the like has recently been attempted, in such uses, replacement of air cells that have been completely discharged is usually performed by ordinary users themselves, and therefore, it is assumed that used air cells are also disposed of by ordinary users. For this reason, for example, air cells that are mainly applied to such uses are required to have a reduced environmental impact so that the air cells can be disposed of safely and with no significant influence on the environment without going through a special process or the like.

In current air cells, aqueous solutions of hydroxides of alkali metals, such as an aqueous solution of potassium hydroxide, which is strongly alkaline, for example, are widely used as electrolytic solutions (Patent Document 1 etc.). On the other hand, depending on the type of the metal material that is used for the negative electrode, there are cases where an aqueous solution with a lower pH (an aqueous solution of sodium chloride, etc.) is used as the electrolytic solution of an air cell (Patent Document 2 etc.), and it is also conceivable to reduce the environmental impact of an air cell through such approaches.

PRIOR ART DOCUMENTS

Patent Documents

Patent Document 1: JP 2016-46116A (paragraph [0068], Examples: paragraph [0073])
Patent Document 2: JP 2016-146257A (paragraph [0015])

DISCLOSURE OF INVENTION

Problem to be Solved by the Invention

However, if an electrolytic solution that has a low pH like an aqueous solution of sodium chloride is used, the characteristics of the air cell will significantly deteriorate compared with a case where a strongly alkaline electrolytic solution is used, and it will be difficult to ensure a practical level of characteristics.

The present invention was made in view of the above-described circumstances, and it is an object thereof to provide an air cell that has a reduced environmental impact and has favorable discharge characteristics, and a patch equipped with the air cell.

Means for Solving Problem

An air cell of the present invention that has achieved the above-described object is an air cell including, an outer case, which contains a positive electrode having a catalyst layer containing a catalyst and a binder, a negative electrode containing a metal material, a separator, and an electrolytic solution, wherein the separator has an air permeability of 10 sec/100 ml or more, and the electrolytic solution is an aqueous solution with a pH of 3 or more and less than 12.

Moreover, another aspect of the air cell of the present invention, which is different from above, is an air cell including, an outer case, which contains a positive electrode having a catalyst layer containing a catalyst and a binder, a negative electrode containing a metal material, a separator, and an electrolytic solution, wherein the positive electrode has a porous sheet made of carbon as a current collector, and the electrolytic solution is an aqueous solution with a pH of 3 or more and less than 12.

Furthermore, a patch of the present invention is a patch that can be worn on the body, the patch including the air cell of the present invention as a power supply.

Effects of the Invention

According to the present invention, it is possible to provide an air cell that has a reduced environmental impact and has favorable discharge characteristics, and a patch equipped with the air cell.

DESCRIPTION OF THE INVENTION

Figure 1:
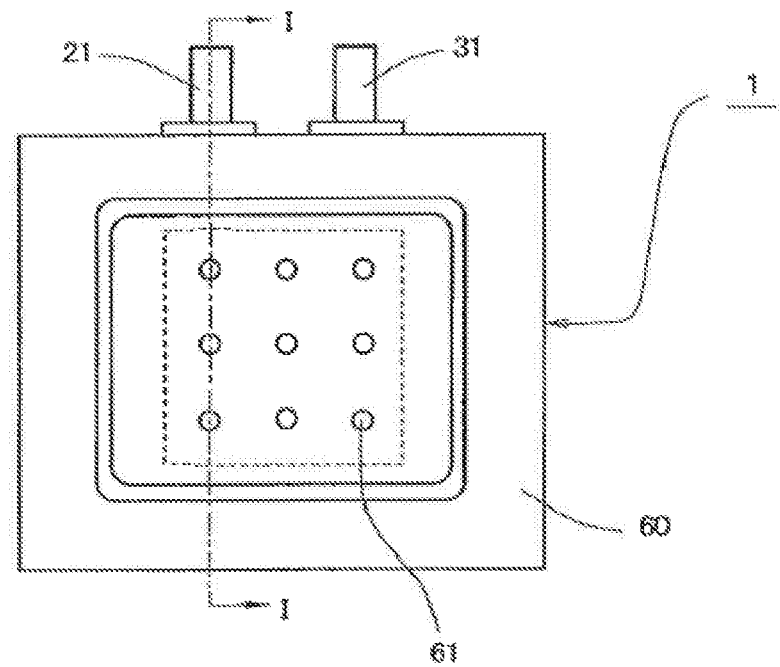
FIG. 1 is a plan view schematically showing an example of an air cell of the present invention.

As described above, when an aqueous solution with a pH of 3 or more and less than 12 is used as the electrolytic solution, although the environmental impact of the air cell can be reduced compared with a case where an aqueous solution with strong alkalinity (with a pH of about 14) such as an aqueous solution of potassium hydroxide, which has conventionally been widely used, is used as the electrolytic solution, the discharge characteristics of the air cell significantly deteriorate.

However, as a result of the study conducted by the inventors of the present invention, it became clear that in an air cell containing an electrolytic solution with a pH of 3 or more and less than 12, if a separator whose air permeability is limited to a certain level, or specifically, a separator having an air permeability of 10 sec/100 ml or more is used as the separator that is disposed between the positive electrode and the negative electrode, the discharge capacity and the discharge voltage can be increased, although the reason is not clear, and therefore, the discharge characteristics significantly improve.

Note that the dependence of the discharge characteristics on the air permeability of the separator is not shown in air cells that have strongly alkaline electrolytic solutions, and is considered to be unique to air cells in which electrolytic solutions with pHs of a certain value or less are used.

The air permeability of the separator used in the air cell of the present invention can be set to be 10 sec/100 ml or more as described above, and is preferably 200 sec/100 ml or more, more preferably 400 sec/100 ml or more, and most preferably 1,000 sec/100 ml or more. Note that it is sufficient that the separator used in the air cell of the present invention is ion-permeable and allows ions necessary for the discharge reaction to pass through, and the upper limit value of the air permeability of the separator is not particularly limited.

As used herein, the air permeability of the separator, and the air permeability of a carbon sheet, which will be described later, are values that are obtained using the Gurley method specified in JIS P 8117.

Separators that satisfy certain conditions can be selected from separators that are adopted in various types of cells including air cells, such as porous membranes (microporous membranes, nonwoven fabrics, and the like) made of resin and semipermeable membranes typified by cellophane films, and can be used as the separator that satisfies the above-described air permeability.

Examples of the resin that constitutes a separator formed of a porous membrane made of resin include polyolefins such as polyethylene (PE), polypropylene (PP), and ethylene-propylene copolymers; polyesters such as polyethylene terephthalate; and the like.

In the case of a separator formed of a porous membrane made of a resin, the air permeability can be adjusted by adjusting the porosity (void fraction) or the tortuousity of pores (voids), for example.

In the case of a separator made of a resin, the porosity thereof is preferably 30% to 80%, and the thickness thereof is preferably 10 to 100 μm.

A semipermeable membrane such as a cellophane film allows only some of the components in the electrolytic solution to pass through, and is therefore favorably used to improve the discharge characteristics in the present invention. In the case where a semipermeable membrane is used as the separator, the separator may be composed only of the semipermeable membrane. However, semipermeable membranes have low strength and are therefore likely to cause problems, such as breakage during the assembly of the cell. For this reason, it is also recommended that the separator be composed of a laminate in which a grafted film composed of a particular polymer and a semipermeable membrane are laminated.

The graft polymer that constitutes the grafted film has a form in which, for example, (meth)acrylic acid or a derivative thereof is graft-polymerized onto a polyolefin (polyethylene, polypropylene, or the like), which serves as a stem polymer. However, it is sufficient that the graft polymer has the above-described form, and the graft polymer need not be a polymer that is produced using the method in which (meth)acrylic acid or a derivative thereof is graft-polymerized onto a polyolefin.

(Meth)acrylic acid or a derivative thereof that constitutes the above-described graft polymer is represented by a general formula (1) below. Note that in the general formula (1) below, $R^1$ means H or $CH_3$, and $R^2$ means H or a hydrophilic substituent such as $NH_4$, Na, K, Rb, or Cs.

Chemical Formula 1

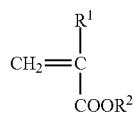

(1)

In the above-described grafted film and cellophane film, the polymers that constitute these films have themselves the function of absorbing the electrolytic solution and allowing ions to pass through.

It is preferable that the graft polymer that constitutes the grafted film has a graft ratio, as defined by an equation (2) below, of 160% or more. Since there is a correlation between the graft ratio of the graft polymer and the electrical resistance of the grafted film, the electrical resistance of the grafted film can be controlled so as to be a preferable value of 20 to 120 mΩ·in² by using a graft polymer whose graft ratio is a value such as that described above. Note that the electrical resistance of the grafted film is a value that is obtained using an AC voltage drop method (1 kHz). The ambient temperature is set at 20 to 25° C., the film is immersed in a 40% KOH (specific gravity: 1.400±0.005) aqueous solution at 25±1° C. and taken out after 5 to 15 hours, and the electrical resistance of that film can be measured.

$$\text{Graft ratio}(\%)=100\times(A-B)/B \qquad (2)$$

In the equation (2) above, A is the mass (g) of the graft polymer and B is the mass (g) of the stem polymer in the graft polymer. Note that, for example, in the case where the graft polymer is formed using the method in which (meth)acrylic acid or a derivative thereof is graft-polymerized onto a polyolefin serving as the stem polymer, "B (mass of the stem polymer in the graft polymer)" in the equation (2) above can be obtained by measuring in advance the mass of the stem polymer used for this graft polymerization. Moreover, the graft ratio of the graft polymer may exceed 100% because there are cases where monomers ((meth)acrylic acid or a derivative thereof) used for graft polymerization are polymerized with one another, resulting in graft molecules having long chains. The upper limit value of the graft ratio of the graft polymer as defined by the equation (2) above is preferably 400%. Note that the above-described "(meth)acrylic acid" refers to acrylic acid and methacrylic acid, collectively.

In the case of a separator composed only of a cellophane film, the thickness thereof is preferably 15 μm or more, and is preferably 40 μm or less and more preferably 30 μm or less, for example.

Furthermore, in the case of a separator composed of a laminate of a grafted film and a cellophane film, the total thickness of the grafted film and the cellophane film is preferably 30 μm or more, and more preferably 40 μm or more, and is preferably 100 μm or less, more preferably 70 μm or less, and most preferably 60 μm or less, for example.

Furthermore, in the case of a separator composed of a laminate of a grafted film and a cellophane film, the thickness of the grafted film is preferably 15 μm or more, and more preferably 25 μm or more, and is preferably 50 μm or less and more preferably 30 μm or less, for example.

Examples of the laminate of a grafted film and a cellophane film for constituting the separator include laminates that are commercially available from Yuasa Membrane Systems Co., Ltd. under the names "YG9132", "YG9122", and "YG2152".

Moreover, the separator may also be composed of a combination of a cellophane film, or a cellophane film and a grafted film, with a liquid-absorbent layer (electrolytic solution retaining layer) like a piece of vinylon-rayon mixed paper. The thickness of such a liquid-absorbent layer is preferably 20 to 500 μm.

The electrolytic solution of the air cell of the present invention is an aqueous solution with a pH of 3 or more, preferably 3.5 or more, more preferably 4 or more, and particularly preferably 5 or more, and less than 12, preferably 10 or less, more preferably 8 or less, and particularly preferably 6.5 or less.

Examples of the electrolyte for constituting the aqueous solution that is used as the electrolytic solution include chlorides, such as sodium chloride, potassium chloride, magnesium chloride, calcium chloride, ammonium chloride, and zinc chloride; hydroxides of alkaline-earth metals (magnesium hydroxide, calcium hydroxide, and the like), acetates (sodium acetate, potassium acetate, magnesium acetate, and the like), nitrates (sodium nitrate, potassium nitrate, magnesium nitrate, and the like), sulfates (sodium sulfate, potassium sulfate, magnesium sulfate, and the like), phosphates (sodium phosphate, potassium phosphate, magnesium phosphate, and the like), borates (sodium borate, potassium borate, magnesium borate, and the like), citrates (sodium citrate, potassium citrate, magnesium citrate, and the like), and glutamates (sodium glutamate, potassium glutamate, magnesium glutamate, and the like); hydrogencarbonates of alkali metals (sodium hydrogencarbonate, potassium hydrogencarbonate, and the like); percarbonates of alkali metals (sodium percarbonate, potassium percarbonate, and the like); compounds containing halogens such as fluorides; polyvalent carboxylic acids; and the like. It is sufficient that the electrolytic solution contains one or two or more electrolytes of these electrolytes.

Note that water-soluble zinc compounds, such as zinc chloride, used for the electrolytic solution of a manganese dry cell, and hydroxides of alkali metals, such as potassium hydroxide, used for the electrolytic solution of an air cell are strongly irritating to the skin, and if the electrolytic solution leaks and adheres to the body, it may cause trouble, such as inflammation, on the skin. For this reason, taking into account the application to a power supply of a medical or healthcare device that is used while being brought into close contact with the body, for example, it is desirable that the electrolytic solution has a configuration that has only a slight influence on the skin.

From the above-described point of view, it is desirable to prevent the electrolytic solution from containing a water-soluble hazardous substance as far as possible, and, for example, it is desirable that the electrolytic solution does not contain compounds designated as "toxic substances". Usually, these compounds when mixed as impurities are not regarded as "toxic substances", but with consideration being given also to such cases, the amount of compounds designated as "toxic substances" contained in the electrolytic solution is desirably 0.5 mass % or less, more desirably 0.1 mass % or less, and particularly desirably 0.01 mass % or less.

Note that the above-described "compounds designated as toxic substances" refer to compounds specified in Appended Table 2 of the "Poisonous and Deleterious Substances Control Law" and Article 2 of the "Cabinet Order for the Enforcement of the Poisonous and Deleterious Substances Control Law" in Japan.

On the other hand, in order to configure an air cell that has excellent discharge characteristics, it is preferable that a salt formed by a strong acid and a weak base is used as the electrolyte. Examples of the strong acid include hydrochloric acid, sulfuric acid, nitric acid, and perchloric acid. Examples of the weak base include hydroxides of metallic elements other than alkali metals, such as aluminum hydroxide and magnesium hydroxide, and ammonia.

Among salts of a strong acid and a weak base, salts of at least one type of ions selected from $Cl^-$, $SO_4^{2-}$, $HSO_4^-$, and $NO_3^-$ and at least one type of ions selected from Al ions, Mg ions, Fe ions, and ammonium ions are preferably used, because these salts have only a slight influence on the skin and can also be disposed of with a reduced environmental impact. Specific examples of the above-described salts include ammonium salts such as ammonium sulfate, ammonium hydrogen sulfate $((NH_4)HSO_4)$, ammonium chloride, and ammonium nitrate; aluminum salts such as aluminum sulfate, aluminum chloride, and aluminum nitrate; magnesium salts such as magnesium sulfate, magnesium chloride, magnesium chloride hydroxide (MgCl(OH)), magnesium nitrate; and iron salts such as iron(II) sulfate, iron(II) ammonium sulfate $((NH_4)_2Fe(SO_4)_2)$, iron(III) sulfate, iron(II) chloride, and iron(II) nitrate. The electrolytic solution may contain two or more electrolytes of these electrolytes.

An aqueous solution containing a salt of a strong acid and a weak base has a relatively weak effect of corroding a metal material, such as zinc or a zinc alloy, serving as the negative electrode active material, when compared with an aqueous solution containing a salt of a strong acid and a strong base, such as sodium chloride. Moreover, an aqueous solution containing a salt of a metallic element selected from Al, Mg, and Fe or an ammonium salt, of salts of strong acids, has a relatively high conductivity compared with, for example, an aqueous solution of zinc chloride. Therefore, when an aqueous solution containing, as the salt of a strong acid and a weak base, a salt of at least one type of ions selected from $Cl^-$, $SO_4^{2-}$, $HSO_4^-$, and $NO_3^-$ and at least one type of ions selected from Al ions, Mg ions, Fe ions, and ammonium ions is used as the electrolytic solution, not only favorable discharge characteristics can be ensured, but also the favorable discharge characteristics can be maintained for a long period of time.

Note that since a salt (iron(III) chloride) of $Cl^-$ ions and $Fe^{3+}$ ions has a strong effect of corroding the metal material serving as the negative electrode active material, compared with salts of the other combinations of ions, it is preferable to use iron(II) chloride $(FeCl_2)$ as a salt of $Cl^-$ ions and Fe ions. Moreover, it is more preferable to use an ammonium salt as a salt of a weak base, because it has a lower effect of corroding the metal material serving as the negative electrode active material.

Moreover, among the salts of strong acids, perchlorates are likely to cause the danger of combustion or explosion when heated or shocked, and therefore, from the standpoints of reducing the environmental impact and ensuring safety during disposal, it is preferable to use a salt other than a perchlorate as the electrolyte, and if the electrolytic solution contains perchloric acid ions, the amount of perchloric acid ions contained is preferably less than 100 ppm and more preferably less than 10 ppm.

Furthermore, among the above-described salts of a strong acid and a weak base, many heavy metal salts (excluding iron salts) typified by zinc chloride, copper sulfate, and the like are hazardous substances, and therefore, in view of the environmental impact and the safety during disposal, also the amount of heavy metal ions, excluding iron ions, contained in the electrolytic solution is preferably less than 100 ppm and more preferably less than 10 ppm.

In order ensure favorable discharge characteristics, the conductivity of the electrolytic solution is preferably 80 mS/cm or more, more preferably 150 mS/cm or more, and particularly preferably 200 mS/cm or more. It is desirable that the concentration of the electrolyte in the electrolytic solution (when only one type of electrolyte is used, the concentration of that electrolyte, and when two or more types of electrolytes are used, the total concentration of these electrolytes) is within a range that can ensure the above-described conductivity. The concentration of the electrolyte in the electrolytic solution is usually about 5 to 50 mass %, and the conductivity of the electrolytic solution can usually be increased to about 700 mS/cm. As used herein, the conductivity of the electrolytic solution means a value that is measured using a method adopted in examples below.

Note that in the case where the concentration of the electrolyte in the electrolytic solution is increased, the concentration of dissolved oxygen, which is related to a corrosion reaction (oxidation reaction) in the electrolytic solution, decreases, and therefore, it can be expected that the corrosion reactions of the metal material serving as the negative electrode active material and the current collector of the positive electrode or the negative electrode can be suppressed more than in the case where an electrolytic solution having a low electrolyte concentration is used. For example, in the case of an aqueous solution of sodium chloride, the effect of corroding metal reaches the maximum at a concentration of 3 mass % (about 0.5 mol/l), but if the electrolyte concentration is increased from this value, the concentration of dissolved oxygen in the electrolytic solution decreases, and the progress of the oxidation reaction of metal is suppressed.

Moreover, if the concentration of the electrolyte in the electrolytic solution is increased, the temperature at which the electrolytic solution solidifies decreases even further due to the effect of freezing point depression, and therefore, an improvement in the discharge characteristics at low temperatures can be expected.

From the above-described points of view, the concentration of the electrolyte in the electrolytic solution (when a plurality of electrolytes are used, the total concentration of these electrolytes; the same holds true for the following description) is preferably 1 mol/l or more, more preferably 2 mol/l or more, and particularly preferably 3 mol/l or more. On the other hand, depending on the type of the electrolyte, if the concentration of the electrolyte in the electrolytic solution approaches the saturation concentration, the ion conductance (conductivity) often decreases conversely, and therefore, the concentration of the electrolyte in the electrolytic solution is preferably 90% or less of the saturation concentration at 20° C., and may be preferably 7 mol/l or less and more preferably 5 mol/l or less, for example.

It is preferable that an indium compound or a tin compound is dissolved in the electrolytic solution. In the case where an indium compound or a tin compound is dissolved in the electrolytic solution, the generation of hydrogen gas within the cell can be more favorably suppressed.

The indium compound and the tin compound dissolved in the electrolytic solution may be hydroxides, oxides, sulfates, sulfides, nitrates, bromides, chlorides, and the like.

The concentration of the compound in the electrolytic solution by mass is preferably 0.005% or more, more preferably 0.01% or more, and particularly preferably 0.05% or more, and is preferably 1% or less, more preferably 0.5% or less, and particularly preferably 0.1% or less.

In addition to the above-described components, various types of known additives may also be added to the electrolytic solution if necessary, as long as the effects of the present invention are not impaired. For example, in order to prevent corrosion (oxidation) of the metal material used for the negative electrode, zinc oxide may be added. Note that zinc oxide may also be added to the negative electrode.

Moreover, although the electrolytic solution may be in liquid form, the electrolytic solution may also be made into so-called gel form using a gelling agent. In the case where an electrolytic solution in gel form is used, the effect of suppressing corrosion of the negative electrode active material is improved even further.

For example, foil of a metal or an alloy serving as the negative electrode active material can be used for the negative electrode as-is. However, in this case, the foil may break due to corrosion caused by the electrolytic solution, impairing the conductivity of the negative electrode, and therefore, the capacity that the negative electrode has may not be sufficiently brought out. Even in the case where such a negative electrode is used, breakage or the like of the foil serving as the negative electrode can be suppressed by using an electrolytic solution having the above-described electrolyte concentration; however, in the case where an electrolyte in gel form is used, the suppression effect is improved even further, and therefore, the decrease in cell capacity can be more favorably suppressed.

Examples of the gelling agent that can be used in the electrolytic solution include polyacrylic acids (polyacrylic acid, sodium polyacrylate, ammonium polyacrylate, and the like) and celluloses (carboxymethyl cellulose, methylcellulose, hydroxypropyl cellulose, alkaline salts of these, and the like). Moreover, as is disclosed in JP 2001-307746A, it is also preferable to use a water-absorbent polymer of cross-linked polyacrylic acid or its salt type (e.g., sodium polyacrylate, ammonium polyacrylate, or the like) together with a gelling agent other than these. The gelling agent that is used together with the water-absorbent polymer of cross-linked polyacrylic acid or its salt type may be the above-described celluloses, cross-linked branched polyacrylic acids or their salts (e.g., a sodium salt, an ammonium salt, and the like), and the like. These gelling agents may be used alone or in a combination of two or more.

Among these gelling agents, a carboxymethyl cellulose (CMC) having a degree of etherification of 1.0 to 1.5 is preferable. The degree of etherification is a numerical value indicating the number of carboxymethyl groups that are ether-linked to a single anhydrous glucose unit. A CMC having the aforementioned degree of etherification has a high effect of increasing the viscosity of the electrolytic solution, and therefore, an electrolytic solution in gel form with even more favorable properties can be easily prepared by using this CMC.

The amount of gelling agent contained in the electrolytic solution is not particularly limited as long as it is an amount that enables the electrolytic solution to be favorably made into gel form, but usually, an amount of about 0.1 to 5 mass % is preferable.

The positive electrode (air electrode) of the air cell has the catalyst layer, and, for example, a positive electrode that has a structure in which the catalyst layer and a current collector are laminated can be used.

The catalyst layer can contain a catalyst, a binder, and so on.

Examples of the catalyst of the catalyst layer include silver, platinum metals or alloys thereof, transition metals, platinum/metal oxides such as $Pt/IrO_2$, perovskite oxides such as $La_{1-x}Ca_xCoO_3$, carbides such as WC, nitrides such as $Mn_4N$, manganese oxides such as manganese dioxide, carbon (graphite, carbon black (acetylene black, Ketjen black, channel black, furnace black, lamp black, thermal black, etc.), charcoal, activated carbon, etc.), and the like, and one or two or more catalysts of these catalysts are used.

Note that it is preferable that the heavy metal content in the catalyst layer, excluding the components of the electrolytic solution, is 1 mass % or less. An air cell that has an even further reduced environmental impact during disposal can be obtained by using a positive electrode having such a catalyst layer.

As used herein, the heavy metal content in the catalyst layer can be measured through fluorescence X-ray analysis. For example, the heavy metal content can be measured using a "ZSX100e" manufactured by Rigaku Corporation under conditions of an excitation source of Rh 50 kV and an analysis area of φ10 mm.

Accordingly, a catalyst containing no heavy metal is recommended as the catalyst of the catalyst layer, and it is more preferable to use the above-described various types of carbon.

Moreover, from the standpoint of increasing the reactivity of the positive electrode even further, the specific surface area of the carbon that is used as the catalyst is preferably 200 $m^2/g$ or more, more preferably 300 $m^2/g$ or more, and even more preferably 500 $m^2/g$ or more. As used herein, the specific surface area of the carbon is a value that is obtained using a BET method in conformity with JIS K 6217, and can be measured using, for example, a specific surface area measuring device ("Macsorb HM model-1201" manufactured by Mountech Co., Ltd.) based on a nitrogen adsorption method. Note that the upper limit value of the specific surface area of the carbon is usually about 2,000 $m^2/g$.

Furthermore, from the standpoint of ensuring the conductivity of the positive electrode, the DBP absorption of the carbon that is used as the catalyst is preferably 150 $cm^3/100$ g or more, more preferably 200 $cm^3/100$ g or more, and even more preferably 300 $cm^3/100$ g or more. As used herein, the DBP absorption of the carbon can be measured in conformity with JIS K 6217 (values described in the examples below are the values that were obtained using this method).

On the other hand, if the DBP absorption is high, the structure develops and the volume of the spaces in the carbon increases, and therefore, the amount of electrolytic solution that is necessary increases. For this reason, the DBP absorption of the carbon used as the catalyst is preferably 1,000 $cm^3/100$ g or less, more preferably 800 $cm^3/100$ g or less, and even more preferably 600 $cm^3/100$ g or less.

The amount of catalyst contained in the catalyst layer is preferably 20 to 70 mass %.

Examples of the binder of the catalyst layer include fluororesin binders such as polymers of vinylidene fluoride (polyvinylidene fluoride (PVDF)), polymers of tetrafluoroethylene (polytetrafluoroethylene (PTFE)), copolymers of vinylidene fluoride and copolymers of tetrafluoroethylene (vinylidene fluoride-hexafluoropropylene copolymer (PVDF-HFP), vinylidene fluoride-chlorotrifluoroethylene copolymer (PVDF-CTFE), vinylidene fluoride-tetrafluoroethylene copolymer (PVDF-TFE), vinylidene fluoride-hexafluoropropylene-tetrafluoroethylene copolymer (PVDF-HFP-TFE), and the like). Among these, polymers or copolymers of tetrafluoroethylene are preferable, and PTFE is more preferable. The amount of binder contained in the catalyst layer is preferably 3 to 50 mass %.

The thickness of the catalyst layer of the positive electrode is preferably 50 to 500 μm.

For example, nets, foil, expanded metal, and punched metal composed of metal materials such as titanium, nickel, stainless steel, and copper; porous sheets made of carbon, such as carbon sheets (carbon sheets composed of fibrous carbon) such as carbon paper, carbon cloth, and carbon felt; and the like can be used as the current collector of the positive electrode.

Note that as a result of the study conducted by the inventors of the present invention, it became clear that when an aqueous solution with a pH of 3 or more and less than 12 is used as the electrolytic solution, apart from the above-described deterioration in discharge characteristics caused by the separator, the discharge characteristics may also deteriorate depending on the material of the current collector of the positive electrode.

That is to say, nets and the like composed of metal materials such as stainless steel are commonly used as the current collectors of the positive electrodes of air cells, and therefore, in the case where an aqueous solution with strong alkalinity (a pH of about 14), such as an aqueous solution of potassium hydroxide, is used as the electrolytic solution, those materials can function as a current collector without any trouble.

However, in the case where an aqueous solution with a lower pH than the above-described strongly alkaline aqueous solution is used as the electrolytic solution, the positive electrode current collector made of metal is more likely to corrode, and the discharge characteristics are more likely to deteriorate in the case where the discharge current increases, for example.

Therefore, in the case where an aqueous solution with a pH of 3 or more and less than 12 is used as the electrolytic solution, it is desirable that a current collector (porous sheet etc.) made of carbon, which does not cause the above-described problem of corrosion, is used as the current collector of the positive electrode, and this makes it possible to suppress the deterioration in discharge characteristics caused by the current collector of the positive electrode.

The above-described carbon sheet may have a single-layer structure, or may have a multilayer structure in which pieces of carbon paper, pieces of carbon cloth, or pieces of carbon felt are laminated or a multilayer structure in which two or more of carbon paper, carbon cloth, and carbon felt are laminated.

Moreover, the carbon sheet and a substrate composed of a material other than carbon may also be integrated and constitute a porous current collector as a whole.

The Gurley value, which indicates the air permeability (in thickness direction) of the carbon sheet is preferably 1 sec/100 ml or more, and more preferably 5 sec/100 ml or more in order to prevent the porosity from excessively increasing and causing a decrease in conductivity. On the other hand, in order to set the porosity to be a certain value or more so as not to obstruct permeation of air, the Gurley value of the carbon sheet is preferably 500 sec/100 ml or less and more preferably 200 sec/100 ml or less.

Moreover, usually, the fiber diameter of the fibrous carbon that constitutes the carbon sheet can be set to be about 2 to 30 μm.

The thickness of the current collector of the positive electrode is preferably 10 to 500 μm, and in view of the ease of handling, the easy availability, the ensuring of a sufficient current-collection function of the positive electrode, and the like, the thickness of the current collector is preferably set to be 30 μm or more, and more preferably 50 μm or more.

From the standpoint of ensuring favorable air-permeability and sufficient strength, the porosity of the above-described carbon sheet is preferably between 50% and 95%, inclusive, and an appropriate carbon sheet can be selected from commercially available products and used.

The catalyst layer can be produced by, for example, mixing the above-described catalyst, binder, and the like with water, rolling the mixture using a roll, and causing the rolled mixture to adhere to the current collector. Moreover, the catalyst layer can also be produced by preparing a catalyst layer-forming composition (slurry, paste, or the like)

by dispersing the above-described catalyst as well as a binder and the like, which are used if necessary, in water or an organic solvent, applying the prepared composition to the surface of the current collector, followed by drying, and then performing press processing, such as calendering, if necessary.

A negative electrode containing a metal material, such as zinc-based materials (zinc materials and zinc alloy materials are collectively called such), magnesium-based materials (magnesium materials and magnesium alloy materials are collectively called such), and aluminum-based materials (aluminum materials and aluminum alloy materials are collectively called such), is used as the negative electrode of the air cell. In this negative electrode, a metal such as zinc, magnesium, or aluminum acts as the active material.

Note that from the standpoint of further reducing the environmental impact of the air cell, it is preferable that the amounts of mercury, cadmium, lead, and chromium contained in the metal material that is used for the negative electrode are small, and specifically, it is more preferable that the mercury content is 0.1% ppm or less, the cadmium content is 0.01% ppm or less, the lead content is 0.1% ppm or less, and the chromium content is 0.1% ppm or less, by mass.

More specifically, for example, negative electrodes containing zinc-based particles (zinc particles and zinc alloy particles are collectively called such), magnesium-based particles (magnesium particles and magnesium alloy particles are collectively called such), aluminum-based particles (aluminum particles and aluminum alloy particles are collectively called such), and the like can be used. The alloying constituents of the zinc alloy particles may be, for example, indium (the amount contained is 0.005% to 0.05% by mass, for example), bismuth (the amount contained is 0.005% to 0.05% by mass, for example), aluminum (the amount contained is 0.001% to 0.15% by mass, for example), and the like.

Moreover, the alloying constituents of the magnesium alloy particles may be, for example, calcium (the amount contained is 1% to 3% by mass, for example), manganese (the amount contained is 0.1% to 0.5% by mass, for example), zinc (the amount contained is 0.4% to 1% by mass, for example), aluminum (the amount contained is 8% to 10% by mass, for example), and the like.

Furthermore, the alloying constituents of the aluminum alloy particles may be, for example, zinc (the amount contained is 0.5% to 10% by mass, for example), tin (the amount contained is 0.04% to 1.0% by mass, for example), gallium (the amount contained is 0.003% to 1.0% by mass, for example), silicon (the amount contained is 0.05% or less by mass, for example), iron (the amount contained is 0.1% or less by mass, for example), magnesium (the amount contained is 0.1% to 2.0% by mass, for example), manganese (the amount contained is 0.01% to 0.5% by mass, for example), and the like.

In the case of a negative electrode containing metal particles, the metal particles may be of a single type, or two or more different types.

With regard to the particle size of zinc-based particles, for example, the ratio of particles with a particle diameter of 75 μm or less to all the particles is preferably 50 mass % or less and more preferably 30 mass % or less, and the ratio of particles with a particle diameter of 100 to 200 μm to all the particles is 50 mass % or more, and more preferably 90 mass % or more.

Moreover, with regard to the particle size of magnesium-based particles and aluminum-based particles, for example, the ratio of particles with a particle diameter of 30 μm or less to all the particles is preferably 50 mass % or less and more preferably 30 mass % or less, and the ratio of particles with a particle diameter of 50 to 200 μm to all the particles is preferably 50 mass % or more and, more preferably 90 mass % or more.

As used herein, the particle size of metal particles is a particle diameter ($D_{50}$) at a volume-based cumulative frequency of 50% as measured by dispersing particles in a medium that does not dissolve these particles, using a laser scattering particle size analyzer (e.g., "LA-920" manufactured by HORIBA Ltd.).

In the case of the negative electrode containing metal particles, the negative electrode may also contain a gelling agent (sodium polyacrylate, carboxymethyl cellulose, etc.) and a binder, which may be added if necessary, and a negative electrode agent (negative electrode in gel form, etc.) that is composed by adding an electrolytic solution thereto can be used. The amount of gelling agent in the negative electrode is preferably 0.5 to 1.5 mass %, for example, and the amount of binder is preferably 0.5 to 3 mass %

The same electrolytic solution as that injected into the cell can be used as the electrolytic solution of the negative electrode containing metal particles.

The amount of metal particles contained in the negative electrode is preferably 60 mass % or more, and more preferably 65 mass % or more and is preferably 95 mass % or less and more preferably 90 mass % or less, for example.

It is preferable that the negative electrode containing metal particles contain an indium compound. As a result of the negative electrode containing an indium compound, generation of hydrogen gas due to the corrosion reaction of the metal particles and the electrolytic solution can be more effectively prevented.

Examples of the aforementioned indium compound include indium oxide, indium hydroxide, and the like.

It is preferable that the amount of indium compound used for the negative electrode is 0.003 to 1 in terms of mass ratio with respect to 100 parts by mass of metal particles.

Moreover, a metal sheet, such as a zinc-based sheet (zinc foil, zinc alloy foil, etc.) having the same composition as the above-described zinc-based particles or a magnesium-based sheet (magnesium foil, magnesium alloy foil, etc.) having the same composition as the above-described magnesium-based particles, can also be used for the negative electrode. In the case of such a negative electrode, the thickness thereof is preferably 10 to 500 μm.

Moreover, in the case of a negative electrode having such a metal sheet, a current collector may also be used, if necessary. The current collector of the negative electrode may be nets, foil, expanded metal, and punched metal made of a metal such as nickel, copper, stainless steel, or the like; sheets and nets of carbon; and the like. The thickness of the current collector of the negative electrode is preferably 10 to 300 μm.

Moreover, in the case where the cell has a sheet-like shape, a carbon paste can also be applied to an inner surface (surface that opposes the negative electrode) of an outer case (sheet-like outer case) of the cell and thereby used as the current collector of the negative electrode. The thickness of the above-described carbon paste layer is preferably 50 to 200 μm.

Furthermore, a metal layer may also be formed on the inner surface of the sheet-like outer case through vapor deposition or the like and used as the current collector of the negative electrode.

There is no particular limitation on the form of the air cell, and any form can be adopted, such as a flat form (including a coin form and a button form) that has a cell case in which an outer can and a sealing plate are sealed together via a gasket through crimping or the outer can and the sealing plate are sealed together through welding; a sheet form that has a sheet-like outer case formed of a resin film; and a tubular form (a cylindrical tubular form and an angular form (angular tubular form)) that has a cell case in which a bottomed-tubular outer can and a sealing plate are sealed together via a gasket or the outer can and the sealing plate are sealed together through welding.

In particular, in the case of an air cell having the above-described sheet-like form, the thickness of the cell can be reduced making it possible to apply to uses where it is difficult to use a cell in a form that has an outer can, and the disposal of the cell is also easier compared with those in the form that has an outer can. Thus, a cell that is suitable as a power supply of a disposable device can be configured.

Moreover, in the case where a resin layer constitutes the inner surface of the sheet-like outer case, the problem of corrosion of the outer case caused by the electrolytic solution can be prevented.

Figure 2:
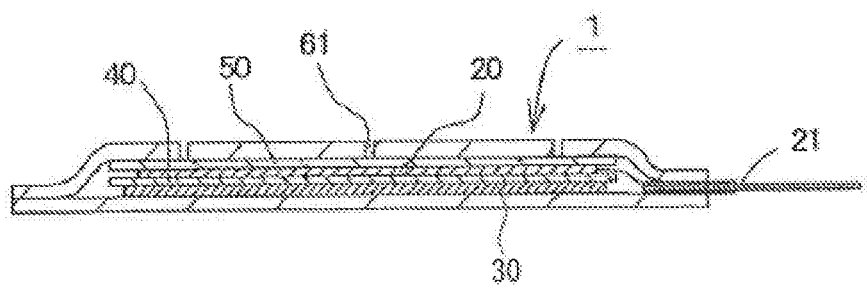
FIG. 2 is a cross-sectional view taken along line I-I in FIG. 1.

FIGS. 1 and 2 schematically show an air cell that has a sheet-like outer case formed of a resin film, as an example of the air cell of the present invention. FIG. 1 is a plan view of the air cell, and FIG. 2 is a cross-sectional view taken along line I-I in FIG. 1.

As shown in FIG. 2, an air cell 1 includes, a sheet-like outer case 60, which contains a positive electrode 20, a separator 40, a negative electrode 30, and an electrolytic solution (not shown). The positive electrode 20 is connected to a positive electrode external terminal 21 via a lead within the cell 1. Moreover, although not shown, the negative electrode 30 is also connected to a negative electrode external terminal 31 via a lead within the cell 1. Note that the dashed lines in FIG. 1 indicate the size of a catalyst layer of the positive electrode 20 accommodated in the sheet-like outer case 60.

A plurality of air holes 61 for taking air into the positive electrode are formed in one face of the sheet-like outer case 60 on the side where the positive electrode 20 is disposed, and a water-repellent membrane 50 for preventing the electrolytic solution from leaking through the air holes 61 is disposed on the sheet-like outer case 60-side of the positive electrode 20.

The positive electrode 20 has a catalyst layer and has, for example, a structure in which the catalyst layer is laminated with a current collector as described above; however, in FIG. 2, in order to avoid complexity of the diagram, the layers of the positive electrode 20 are not separately shown.

The resin film that constitutes the sheet-like outer case may be a nylon film (nylon 66 film etc.), a polyester film (polyethylene terephthalate (PET) film etc.), or the like. The thickness of the resin film is preferably 20 to 100 µm.

Note that, in general, the sheet-like outer case is sealed through thermal fusion bonding of an end portion of the resin film that is located on the upper side of the sheet-like outer case and an end portion of the resin film that is located on the lower side; however, for the purpose of further facilitating the thermal fusion bonding, it is also possible to laminate a thermal fusion-bondable resin layer on the above-exemplified resin film and use the resulting laminate for the sheet-like outer case. Examples of the thermal fusion bondable resin that constitutes the thermal fusion bondable resin layer include modified polyolefin films (modified polyolefin ionomer film etc.), polypropylene and copolymers thereof, and the like. The thickness of the thermal fusion bondable resin layer is preferably 20 to 100 µm.

Moreover, a metal layer may also be laminated on the resin film. The metal layer may be composed of an aluminum film (aluminum foil, including aluminum alloy foil), a stainless steel film (stainless steel foil), or the like. The thickness of the metal layer is preferably 10 to 150 µm.

Moreover, the resin film that constitutes the sheet-like outer case may be a film having a configuration in which the above-described thermal fusion bondable resin layer and the above-described metal layer are laminated.

The shape of the sheet-like outer case may be a polygon (triangle, quadrangle, pentagon, hexagon, heptagon, or octagon) in plan view or may be a circle or an ellipse in plan view. Note that in the case of a sheet-like outer case that has a polygonal shape in plan view, the positive electrode external terminal and the negative electrode external terminal may be led out from the same side, or may individually be led out from different sides.

A membrane capable of allowing air to pass through while having water repellency is used as the water-repellent membrane of the air cell. Specifically, for example, a membrane composed of a resin, such as a fluororesin such as PTFE; a polyolefin such as polypropylene or polyethylene; or the like, can be used. The thickness of the water-repellent membrane is preferably 50 to 250 µm.

In the air cell, an air diffusion membrane for supplying air taken in the outer case to the positive electrode may also be disposed between the outer case and the water-repellent membrane. A nonwoven fabric composed of a resin such as cellulose, polyvinyl alcohol, polypropylene, or nylon can be used as the air diffusion membrane. The thickness of the air diffusion membrane is preferably 100 to 250 µm.

Moreover, in the case where an outer case in a form in which sealing is performed through crimping is used, polypropylene, nylon, or the like can be used as the material of the gasket that is disposed between the outer can and the sealing plate. In addition, in the case where heat resistance is required depending on the use of the cell, it is also possible to use a heat-resistant resin with a melting point of more than 240° C., such as a fluororesin such as tetrafluoroethylene-perfluoroalkoxyethylene copolymer (PFA), polyphenylene ether (PPE), polysulfone (PSF), polyarylate (PAR), polyether sulfone (PES), polyphenylene sulfide (PPS), polyetheretherketone (PEEK), or the like. Moreover, in the case where the cell is applied to uses where heat resistance is required, a glass hermetic seal can also be used for sealing.

The air cell of the present invention has a reduced environmental impact, and even when the electrolytic solution thereof leaks due to breakage or the like and adheres to the body, it is less likely to cause problems compared with, for example, a strongly alkaline electrolytic solution with a higher pH. Accordingly, the air cell of the present invention is suitable as a power supply of devices intended for medical or healthcare purposes, such as a patch that can be worn on the body, in particular, a patch that is worn on the surface of the skin and used to perform measurement related to the conditions of the body, such as the body temperature, the pulse, and the amount of perspiration.

EXAMPLES

Hereinafter, the present invention will be described in detail based on examples. However, the following examples should not be construed as limiting the present invention.

Example 1

Positive Electrode

Carbon A (Ketjen black EC600JD (Lion Specialty Chemicals Co., Ltd.)) in an amount of 75 parts by mass, the carbon A having a DBP absorption of 495 cm$^3$/100 g and a specific surface area of 1270 m$^2$/g, PTFE in an amount of 25 parts by mass, and water were mixed and rolled to form a sheet for a catalyst layer. Next, this sheet was crimped onto a current collector formed of a 700-mesh metal net (wire diameter: 0.1 mm, thickness: 0.25 mm) made of SUS 304, followed by drying. Then, the sheet was punched into a shape having the catalyst layer with a size of 30 mm×30 mm and also having an exposed portion of the current collector at one end. Furthermore, a nickel lead wire was welded to the exposed portion of the current collector to form a lead portion. Thus, a positive electrode (air electrode) having a total thickness of 300 μm was produced.

Negative Electrode

A piece of zinc alloy foil (thickness: 0.05 mm) containing In in an amount of 0.05%, Bi in an amount of 0.04%, and Al in an amount of 0.001% as additional elements was punched into a shape having a 30 mm×30 mm portion serving as the main body of a negative electrode, and also having, at one end thereof a 5 mm×15 mm portion serving as a lead portion of the negative electrode. Thus, the negative electrode was produced.

Electrolytic Solution

A 20 mass % aqueous solution of sodium chloride (pH=7) was used as an electrolytic solution. The amount of perchloric acid ions contained in this electrolytic solution and the amount of heavy metal ions, excluding iron ions, contained therein were individually less than 100 ppm, and the amount of compounds designated as toxic substances contained in this electrolytic solution was less than 10 ppm.

Separator

Two grafted films (thickness per film: 15 μm) composed of a graft copolymer having a structure in which acrylic acid was graft-polymerized onto the polyethylene main chain were arranged on opposite sides of a cellophane film (thickness: 20 μm), and a piece of vinylon-rayon mixed paper (thickness: 300 μm) was further laminated thereon. The resulting laminate was used as a separator.

Water-Repellent Membrane

A PTFE sheet having a thickness of 200 μm was used as a water-repellent membrane.

Cell Assembly

Two 5 cm×5 cm aluminum laminate films (thickness: 65 μm) each having a PET film on an outer surface of a piece of aluminum foil and a polypropylene film serving as a thermal fusion bondable resin layer on an inner surface of the aluminum foil were used to compose an outer case.

In the aluminum laminate film on the positive electrode side of the outer case, nine air holes with a diameter of 1 mm were formed in advance in a regular pattern at equal intervals of 9 mm in length×9 mm in width (the center-to-center distance of the air holes was 10 mm) so that the air holes were arranged in a similar manner to that shown in FIG. 1, relative to the catalyst layer of the positive electrode. Then, the above-described water-repellent membrane was thermally fused on an inner surface side of the aluminum laminate film using a hot melt resin.

Next, the positive electrode, the separator, and the negative electrode were laminated in that order on the water-repellent membrane set on the aluminum laminate film. Furthermore, the other aluminum laminate film was laid thereon. The two aluminum laminate films were heat-sealed to each other on three peripheral sides (other than the side from which the lead wires were led out) through thermal fusion to form a bag-like shape, and the electrolytic solution was injected from an opening portion thereof. Then, the opening portion was sealed through thermal fusion, to thereby obtain a sheet-like air cell.

Note that in order to increase the sealing properties of a thermal fusion portion between the lead wires of the positive and negative electrodes and the outer case, the thermal fusion was performed after tape-like polypropylene was attached to the lead wires in advance.

Example 2

A sheet-like air cell was produced in a similar manner to that in Example 1 except that carbon B (furnace black) having a DBP absorption of 131 cm$^3$/100 g and a specific surface area of 140 m$^2$/g was used instead of the carbon A (Ketjen black) in forming the sheet for the catalyst layer.

Example 3

A sheet-like air cell was produced in a similar manner to that in Example 1 except that the sheet for the catalyst layer was formed by mixing the carbon A (Ketjen black) in an amount of 50 parts by mass, manganese dioxide in an amount of 25 parts by mass, PTFE in an amount of 25 parts by mass, and water and rolling the mixture.

Example 4

A sheet-like air cell was produced in a similar manner to that in Example 1 except that a PE microporous film (thickness: 30 μm, porosity: 50%) was used as the separator.

Example 5

A sheet-like air cell was produced in a similar manner to that in Example 1 except that a 20 mass % aqueous solution of magnesium sulfate (pH=5) was used as the electrolytic solution.

Comparative Example 1

A sheet-like air cell was produced in a similar manner to that in Example 1 except that only a piece of vinylon-rayon mixed paper (thickness: 300 μm) was used as the separator.

Comparative Example 2

A sheet air cell was produced in a similar manner to that in Example 1 except that a 30 mass % aqueous solution of potassium hydroxide (pH=14) was used as the electrolytic solution.

Comparative Example 3

A sheet-like air cell was produced in a similar manner to that in Comparative Example 2 except that only a piece of vinylon-rayon mixed paper (thickness: 300 μm) was used as the separator.

The sheet-like air cells of the examples and the comparative examples, as well as the electrolytic solutions and the positive electrodes that were used in these cells were evaluated as follows. Table 1 shows the results of the evaluations and the configurations of the respective cells.

Measurement of pH of Electrolytic Solution

The pH of the electrolytic solutions was measured in an environment at 25° C. using a "LAQUA Twin compact pH meter" manufactured by HORIBA Ltd.

Measurement of Amount of Heavy Metal in Catalyst Layer of Positive Electrode

The amount of heavy metals in the catalyst layers of the positive electrodes was measured through fluorescence X-ray analysis. After the materials were mixed and the mixture was rolled to form the sheet for the catalyst layer, the sheet was dried at 60° C. for 24 hours, punched into a shape with φ10 mm, and used as a measurement sample With respect to each of the thus obtained measurement samples, the amount of heavy metals was measured under the conditions of an excitation source of Rh 50 kV and an analysis area of φ10 mm, using a "ZSX100e" manufactured by Rigaku Corporation.

Evaluation of Discharge Characteristics

After each sheet-like air cell was assembled, the cell was allowed to stand in the atmosphere for 10 minutes and then discharged to 0.5 V at a current corresponding to the 100 hour rate with respect to the design capacity (capacity of the negative electrode) of the cell. The discharge capacity at that time was measured. The measurement values of the cells were compared relative to the discharge capacity of the cell of Comparative Example 2, which was taken as 1.0.

chloride with a pH of 7 or the aqueous solution of magnesium sulfate with a pH of 5 was used as the electrolytic solutions, the separators with an air permeability of 10 sec/100 ml or more were used. Thus, these sheet-like air cells exhibited a highly practical, excellent discharge capacity as is the case with the cell of Comparative Example 3, in which the aqueous solution of potassium hydroxide with a pH of 14 was used as the electrolytic solution. Note that a comparison between the cell of Example 1 and the cell of Example 2 showed that the cell of Example 1, in which the carbon having a higher specific surface area and a higher DBP absorption was used as the catalyst of the positive electrode, exhibited a superior discharge capacity to that of the cell of Example 2.

Moreover, as is clear from a comparison between the discharge capacities of the cells of Comparative Examples 2 and 3, the air cells in which the aqueous solution of potassium hydroxide with a pH of 14 was used as the electrolytic solutions showed little difference in cell characteristics attributable to the difference in air permeability between the separators, whereas with respect to the cells of Examples 1 and 4 as well as Comparative Example 1, in which the aqueous solution of sodium chloride with a pH of 7 was used as the electrolytic solutions, the results showed the dependence of the discharge capacity on the air permeability of the separator.

TABLE 1

| | Electrolytic solution | | Catalyst layer of positive electrode | | Separator | | Discharge capacity of cell |
|---|---|---|---|---|---|---|---|
| | Type | pH | Configuration | Amount of heavy metal (mass %) | Configuration | Air permeability (sec/100 ml) | |
| Ex. 1 | Aqueous solution of sodium chloride | 7 | Carbon A PTFE | <1 | Grafted film Cellophane film Mixed paper | >2000 | 1.0 |
| Ex. 2 | Aqueous solution of sodium chloride | 7 | Carbon B PTFE | <1 | Grafted film Cellophane film Mixed paper | >2000 | 0.7 |
| Ex. 3 | Aqueous solution of sodium chloride | 7 | Carbon A Manganese dioxide PTFE | 10 | Grafted film Cellophane film Mixed paper | >2000 | 1.0 |
| Ex. 4 | Aqueous solution of sodium chloride | 7 | Carbon A PTFE | <1 | PE microporous film | 530 | 0.9 |
| Ex. 5 | Aqueous solution of magnesium sulfate | 5 | Carbon A PTFE | <1 | Grafted film Cellophane film Mixed paper | >2000 | 1.1 |
| Com. Ex. 1 | Aqueous solution of sodium chloride | 7 | Carbon A PTFE | <1 | Mixed paper | 1 | 0.2 |
| Com. Ex. 2 | Aqueous solution of potassium hydroxide | 14 | Carbon A PTFE | <1 | Grafted film Cellophane film Mixed paper | >2000 | 1.0 |
| Com. Ex. 3 | Aqueous solution of potassium hydroxide | 14 | Carbon A PTFE | <1 | Mixed paper | 1 | 0.9 |

As shown in Table 1, in the sheet-like air cells of Examples 1 to 5, although the aqueous solution of sodium Based on these results, it is found that the use of a separator with low air permeability (with a high air permeability value) in an air cell that uses an electrolytic solution with a pH of less than 12, which is lower than the pH of electrolytic solutions that have conventionally been widely used in air cells, is effective in improving the discharge characteristics.

Example 6

Positive Electrode

A positive electrode was produced using a piece of porous carbon paper (thickness: 0.25 mm, porosity: 75%, air permeability (Gurley): 70 sec/100 ml) as a current collector.

A catalyst layer-forming composition was formed by mixing the above-described carbon A in an amount of 30 parts by mass, an acrylic dispersant in an amount of 15 parts by mass, SBR in an amount of 60 parts by mass, and water in an amount of 500 parts by mass. This composition was applied in stripes to the surface of the current collector such that the amount thereof after drying was 10 mg/cm$^2$, followed by drying. Then, the resulting sheet after drying was punched into a shape having the catalyst layer with a size of 15 mm×15 mm and also having an exposed portion (with a size of 5 mm×15 mm) of the current collector at one end, the exposed portion serving as a lead portion. Thus, the positive electrode (air electrode) having a total thickness of 0.27 mm was produced.

Negative Electrode

A negative electrode was produced by punching a piece of the same zinc alloy foil as that of Example 1 into a shape having a 15 mm×15 mm portion serving as the main body of the negative electrode, and also having a 5 mm×15 mm portion serving as a lead portion at one end.

Electrolytic Solution

An aqueous solution of sodium chloride (pH=7) with a concentration of 3 mol/l was used as an electrolytic solution. The amount of perchloric acid ions contained in this electrolytic solution and the amount of heavy metal ions, excluding iron ions, contained therein were individually less than 100 ppm, and the amount of compounds designated as toxic substances contained in the electrolytic solution was less than 10 ppm.

Separator

Two grafted films (thickness per film: 15 μm) composed of a graft copolymer having a structure in which acrylic acid was graft-polymerized onto the polyethylene main chain were arranged on opposite sides of a cellophane film (thickness: 20 μm), and the thus obtained laminate (total thickness: 50 μm) was used as a separator. The air permeability of this separator was a value greater than 2,000 sec/100 ml.

Water-Repellent Membrane

A PTFE sheet having a thickness of 200 μm was used as a water-repellent membrane.

Cell Assembly

Two 25 mm×25 mm aluminum laminate films (thickness: 65 μm) each having a PET film on an outer surface of a piece of aluminum foil and a polypropylene film serving as a thermal fusion bondable resin layer on an inner surface of the aluminum foil were used to compose an outer case.

Subsequently, similar procedures to those in Example 1 were performed to produce a sheet-like air cell having a thickness of 0.8 mm. Note that, as in Example 1, in the aluminum laminate film on the positive electrode side of the outer case, nine air holes with a diameter of 0.5 mm were formed in advance in a regular pattern at equal intervals of 4.5 mm in length×4.5 mm in width (the center-to-center distance of the air holes was 5 mm). Moreover, the amount of electrolytic solution injected into the inside of the outer case was 0.1 ml.

Example 7

A sheet-like air cell was produced in a similar manner to that in Example 6 except that the current collector of the positive electrode was changed to a 700-mesh metal net (wire diameter: 0.1 mm, thickness: 0.25 mm) made of SUS 304.

Comparative Example 4

A sheet-like air cell was produced in a similar manner to that in Example 6 except that a 30 mass % aqueous solution of potassium hydroxide (pH=14) was used as the electrolytic solution.

Comparative Example 5

A sheet-like air cell was produced in a similar manner to that in Example 7 except that a 30 mass % aqueous solution of potassium hydroxide (pH=14) was used as the electrolytic solution.

After the sheet-like air cells of Examples 6 and 7 as well as Comparative Examples 4 and 5 were assembled, the cells were allowed to stand in the atmosphere for 10 minutes, and then evaluated as follows.

Measurement of Open-Circuit Voltage

The open-circuit voltage of each cell was measured using a digital multimeter manufactured by Hioki E.E. Corporation.

Measurement of Discharge Capacity

The cell was discharged to 0.5 V by performing constant resistance discharge at 3.9 kΩ, and the discharge capacity at that time was measured. Moreover, volumetric energy density was calculated from the obtained discharge capacity.

Evaluation of Load Characteristics

Another cell that was different from the one discharged at a constant resistance of 3.9 kΩ was discharged at a constant resistance of 0.75 kΩ. The constant resistance discharge was performed to 0.5 V, and the discharge capacity at that time was measured. Then, the ratio (capacity retention rate) of the discharge capacity at 0.75 kΩ to the discharge capacity at 3.9 kΩ was calculated, and the load characteristics were evaluated.

Table 2 shows the results of the above-described evaluations.

TABLE 2

| | Voltage (V) | Discharge capacity (mAh) | Volumetric energy density (Wh/l) | Capacity retention rate (%) |
|---|---|---|---|---|
| Ex. 6 | 1.2 | 30 | 72 | 80 |
| Ex. 7 | 1.1 | 5 | 11 | 50 |
| Com. Ex. 4 | 1.4 | 33 | 93 | 88 |
| Com. Ex. 5 | 1.4 | 31 | 88 | 84 |

As shown in Table 2, in the sheet-like air cell of Example 6, in which the aqueous solution of sodium chloride (pH=7) was used as the electrolytic solution, and the carbon paper, which is a porous carbon sheet, was used as the current collector of the positive electrode, corrosion of the current collector caused by the electrolytic solution was prevented. Therefore, compared with the cell of Example 7, in which a general-purpose metal net was used as the current collector of the positive electrode, the cell of Example 6 had a higher discharge capacity, that is, a higher volumetric energy density and also had superior load characteristics.

On the other hand, as is clear from the evaluation results of the cells of Comparative Examples 4 and 5, in the cells in which the strongly alkaline aqueous solution was used as the electrolytic solutions, there were only small differences in characteristics attributable to the materials of the current collectors of the positive electrodes, and the problem of corrosion of the current collectors caused by the electrolytic solutions hardly occurred.

Examples 8 to 16

Electrolytic solutions shown in Table 3 were prepared by varying the type of the salt serving as the electrolyte and the concentration of the salt, and sheet-like air cells were produced in a similar manner to that in Example 6 except that the thus prepared electrolytic solutions were used. Prior to the cell assembly, the conductivity of each of the electrolytic solutions was measured in an environment at 25° C. using a "Personal SC Meter SC72" manufactured by Yokogawa Electric Corporation.

Note that in all of the electrolytic solutions except for Example 16, the amount of perchloric acid ions contained and the amount of heavy metal ions, excluding iron ions, contained were individually less than 100 ppm.

TABLE 3

| | Electrolytic Solution | | | |
|---|---|---|---|---|
| | Electrolyte | | | |
| | Type | Concentration (mol/l) | pH | Conductivity (mS/cm) |
| Ex. 8 | Sodium chloride | 3.4 | 7.0 | 220 |
| Ex. 9 | Sodium chloride | 1.6 | 7.0 | 100 |
| Ex. 10 | Sodium chloride | 0.9 | 7.0 | 40 |
| Ex. 11 | Ammonium chloride | 3.9 | 4.3 | 375 |
| Ex. 12 | Ammonium sulfate | 1.6 | 5.3 | 180 |
| Ex. 13 | Iron(III) sulfate | 0.5 | 3.2 | 40 |
| Ex. 14 | Sodium acetate | 2.4 | 4.7 | 25 |
| Ex. 15 | Ammonium acetate | 2.3 | 4.0 | 20 |
| Ex. 16 | Zinc chloride | 1.5 | 5.1 | 95 |

After the sheet-like air cells of Examples 8 to 12 were assembled, the cells were allowed to stand in the atmosphere for 10 minutes, and then, the above-described "measurement of open-circuit voltage", "measurement of discharge capacity", and "evaluation of load characteristics" were performed. Moreover, the discharge capacity of the sheet-like air cells of Examples 13 to 16 was measured through constant resistance discharge at 3.9 kΩ.

Table 4 shows the results of the measurements.

TABLE 4

| | Voltage (V) | Discharge capacity (mAh) | Volumetric energy density (Wh/l) | Capacity retention rate (%) |
|---|---|---|---|---|
| Ex. 8 | 1.2 | 30 | 72 | 80 |
| Ex. 9 | 1.1 | 23 | 55 | 60 |
| Ex. 10 | 1.1 | 5 | 11 | 20 |
| Ex. 11 | 1.2 | 33 | 79 | 95 |
| Ex. 12 | 1.2 | 35 | 84 | 90 |
| Ex. 13 | — | 23 | — | — |
| Ex. 14 | — | 6 | — | — |

TABLE 4-continued

| | Voltage (V) | Discharge capacity (mAh) | Volumetric energy density (Wh/l) | Capacity retention rate (%) |
|---|---|---|---|---|
| Ex. 15 | — | 4 | — | — |
| Ex. 16 | — | 19 | — | — |

Based on the evaluation results of the sheet-like cells of Examples 8 to 12, it is found that the discharge capacity of a cell is increased, and the load characteristics are also improved, by setting the conductivity of the electrolytic solution to be 80 mS/cm or more, or in particular, 150 mS/cm or more.

Moreover, the cell of Example 13, in which iron(III) sulfate, which is a salt of a strong acid and a weak base, was used as the electrolyte, exhibited a relatively high discharge capacity even though the conductivity of the electrolytic solution was as low as 40 mS/cm, and thus exhibited superior characteristics to those of the cells of Example 10, in which sodium chloride (a salt of a strong acid and a strong base) was used, Example 14, in which sodium acetate (a salt of a weak acid and a strong base) was used, and Example 15, in which ammonium acetate (a salt of a weak acid and a weak base) was used, though the electrolytic solutions of these cells had approximately the same conductivity as that of the cell of Example 13.

Moreover, although the conductivity of the electrolytic solution of the cell of Example 13, in which an iron salt was used, was lower than that of the cell of Example 16, in which zinc chloride, which is neither an ammonium salt, an aluminum salt, a magnesium salt, nor an iron salt, of salts of strong acids and weak bases, the cell of Example 13 achieved a higher discharge capacity than the cell of Example 16. Therefore, it is found that the cell characteristics can be improved even further by using a particular salt as the electrolyte.

The present invention may be embodied in other forms without departing from the gist thereof. The embodiments disclosed in this application are to be considered in all respects as illustrative, and the present invention is not limited to these embodiments. The scope of the present invention is indicated by the appended claims rather than by the foregoing description of the specification, and all changes which come within the meaning and range of equivalency of the claims are intended to be embraced therein.

INDUSTRIAL APPLICABILITY

As described above, the air cell of the present invention is suitable as a power supply of devices intended for medical or healthcare purposes, such as a patch that can be worn on the body, and can also be applied to uses where conventionally known air cells are adopted.

LIST OF REFERENCE NUMERALS

1 Air cell
20 Positive electrode (Air electrode)
21 Positive electrode external terminal
30 Negative electrode
31 Negative electrode external terminal
40 Separator
50 Water-repellent membrane
60 Sheet-like outer case
61 Air hole

The invention claimed is:

1. An air cell comprising, an outer case, which contains a positive electrode having a catalyst layer containing a catalyst and a binder, a negative electrode containing a metal material, a separator, and an electrolytic solution containing an electrolyte,
wherein the negative electrode is formed of a metal sheet,
the separator has an air permeability of 10 sec/100 ml or more,
the electrolytic solution is an aqueous solution with a pH of 3 or more and less than 12, and
a concentration of the electrolyte in the electrolytic solution is 1 mol/l or more.

2. The air cell according to claim 1, comprising a semipermeable membrane or a microporous membrane made of polyolefin as the separator.

3. The air cell according to claim 1, wherein the electrolytic solution contains a salt of a strong acid and a weak base, as the electrolyte.

4. The air cell according to claim 3, wherein at least one salt selected from an ammonium salt, an aluminum salt, a magnesium salt, and an iron salt is contained as the salt of a strong acid and a weak base.

5. The air cell according to claim 1, wherein the concentration of the electrolyte in the electrolytic solution is 2 mol/l or more.

6. The air cell according to claim 1, wherein the positive electrode has a porous sheet made of carbon as a current collector.

7. The air cell according to claim 1, wherein the outer case is formed of a resin film.

8. A patch that can be worn on the body, the patch comprising the air cell according to claim 1 as a power supply.

9. The air cell according to claim 1, wherein the metal sheet includes a main body and a lead portion.

10. The air cell according to claim 1, wherein the metal sheet is a zinc foil or a zinc alloy foil.

11. The air cell according to claim 1, wherein a thickness of the metal sheet is 10 to 500 μm.

12. The air cell according to claim 1, wherein the pH of the electrolytic solution is 6.5 or less.

13. An air cell comprising, an outer case, which contains a positive electrode having a catalyst layer containing a catalyst and a binder, a negative electrode containing a metal material, a separator, and an electrolytic solution containing an electrolyte,
wherein the positive electrode has a porous sheet made of carbon as a current collector,
the electrolytic solution is an aqueous solution with a pH of 3 or more and less than 12, and
a concentration of the electrolyte in the electrolytic solution is 1 mol/l or more.

14. The air cell according to claim 13, wherein the electrolytic solution contains a salt of a strong acid and a weak base, as the electrolyte.

15. The air cell according to claim 14, wherein at least one salt selected from an ammonium salt, an aluminum salt, a magnesium salt, and an iron salt is contained as the salt of a strong acid and a weak base.

16. The air cell according to claim 13, wherein the concentration of the electrolyte in the electrolytic solution is 2 mol/l or more.

17. The air cell according to claim 13, wherein a Gurley value of the porous sheet made of carbon is 500 sec/100 ml or less.

18. The air cell according to claim 13, wherein a porosity of the porous sheet made of carbon is between 50% and 95%.

19. The air cell according to claim 13, wherein the pH of the electrolytic solution is 6.5 or less.

20. The air cell according to claim 13, wherein the porous sheet made of carbon includes a portion where the catalyst layer is formed and a lead portion where the catalyst layer is not formed.

* * * * *